US00PP25849P3

(12) United States Plant Patent
Larse

(10) Patent No.: US PP25,849 P3
(45) Date of Patent: Sep. 1, 2015

(54) STRAWBERRY PLANT NAMED 'LILI'

(50) Latin Name: *Fragaria×ananassa*
Varietal Denomination: LILI

(71) Applicant: Sweet Darling Sales, Inc., Aptos, CA (US)

(72) Inventor: John Larse, Aptos, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 139 days.

(21) Appl. No.: 13/986,674

(22) Filed: May 23, 2013

(65) Prior Publication Data

US 2013/0340134 P1 Dec. 19, 2013

Related U.S. Application Data

(60) Provisional application No. 61/650,798, filed on May 23, 2012.

(51) Int. Cl.
*A01H 5/00* (2006.01)
*A01H 5/08* (2006.01)

(52) U.S. Cl.
USPC ..... Plt./209
CPC ..... *A01H 5/0893* (2013.01)

(58) Field of Classification Search
USPC ..... Plt./209
See application file for complete search history.

*Primary Examiner* — Annette Para
(74) *Attorney, Agent, or Firm* — Cooley LLP

(57) ABSTRACT

The present invention provides a new and distinct strawberry variety designated as 'LILI' (a.k.a., '101983').

7 Drawing Sheets

Latin name of genus and species: *Fragaria×ananassa.*
Varietal denomination: 'LILI' or 'LILY'.

BACKGROUND OF THE INVENTION

The present invention relates to a new and distinct early day-neutral strawberry variety designated as 'LILI' (a.k.a. '101983', or 'LILY'). This new variety is the result of a controlled-cross between two proprietary cultivars made by the Inventor and was first fruited in Watsonville, Calif. growing fields. The identities of the two parental cultivars were inadvertently lost during the breeding process, but 'LILI' was identified and selected as a new and distinctive variety from a cultivated area where the off-spring derived from the cross were planted. No other sibling from the cross between these two parental proprietary cultivars was collected.

Following selection and during testing, the plant was originally designated '101983' and subsequently named 'LILI'. The new variety of 'LILI' was asexually reproduced via runners (stolons) by the inventor at Watsonville, Calif. Asexual propagules from the original source have been tested in the Watsonville growing fields and, to a limited extent, growing fields in low and high elevation. The properties of this variety were found to be transmissible by such asexual reproduction. The cultivar is stable and reproduces true to type in successive generations of asexual reproduction.

SUMMARY OF THE INVENTION

This invention relates to a new and distinctive early producing day-neutral type cultivar designated as 'LILI'. It is primarily adapted to the climate and growing conditions of the central coast of California. This region provides the necessary temperatures required for it to produce a strong vigorous plant and to remain in fruit production from April through October. The nearby Pacific Ocean provides the needed humidity and moderate day temperatures and evening chilling to maintain fruit quality for the production months.

The following traits in combination distinguish strawberry variety 'LILI' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

The following are the most outstanding and distinguishing characteristics of this new variety when grown under normal conditions in Watsonville, Calif.

Large fruit;
High yield; and
Early harvest interval.

When 'LILI' is compared to 'Albion' (U.S. Plant Pat. No. 16,228), it produces significantly larger fruit in moderate quantities. 'LILI' tends to be early, producing fruit for a few weeks before 'Albion's' first harvest.

DESCRIPTION OF THE DRAWINGS

The accompanying color photographs depict various characteristics of the 'LILI' cultivar at various stages of development as nearly true as possible to make color reproductions.

DETAILED BOTANICAL DESCRIPTION

Figure 1:
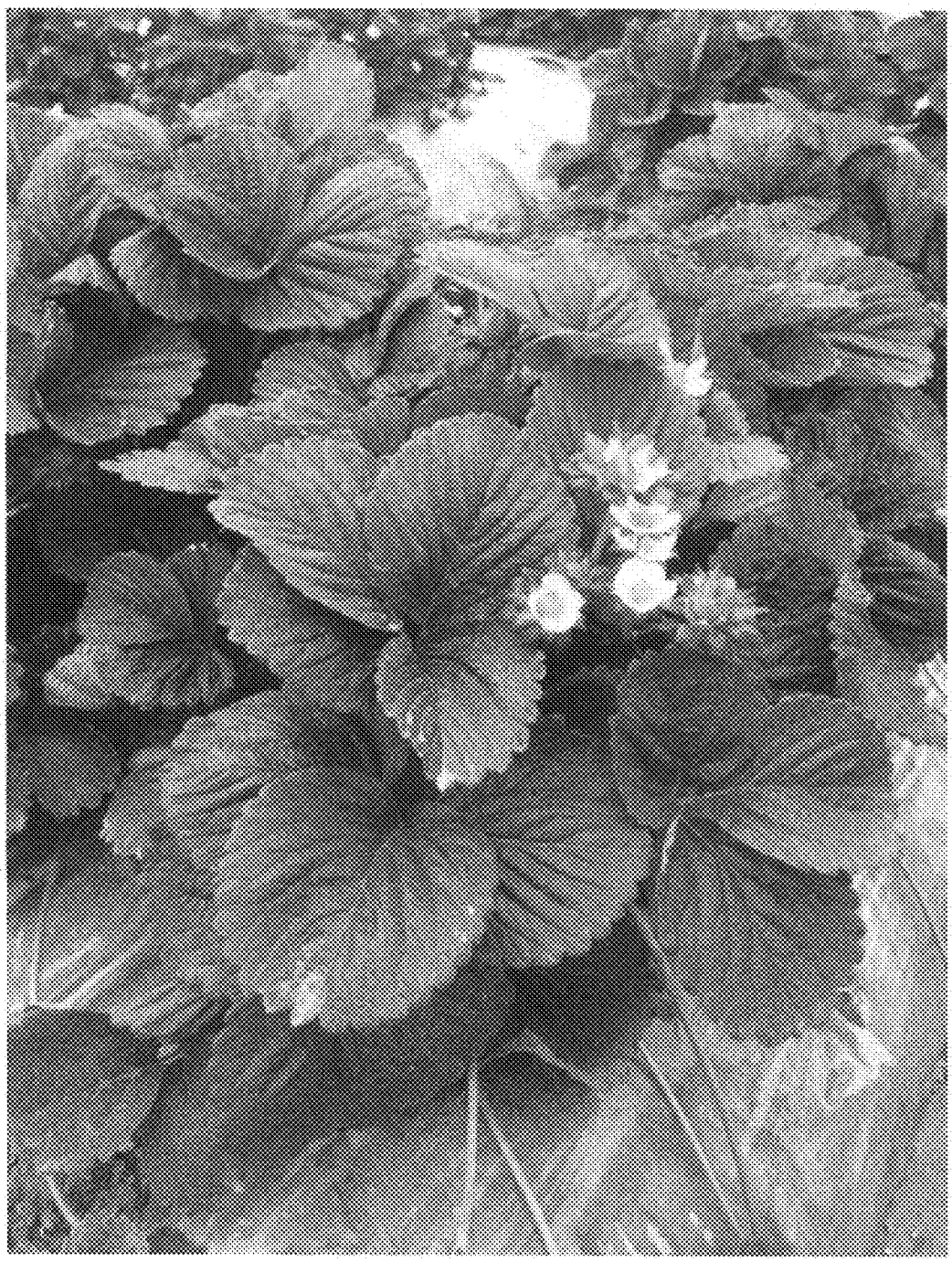
FIG. 1 shows 'LILI' plant in early May.
Figure 2:
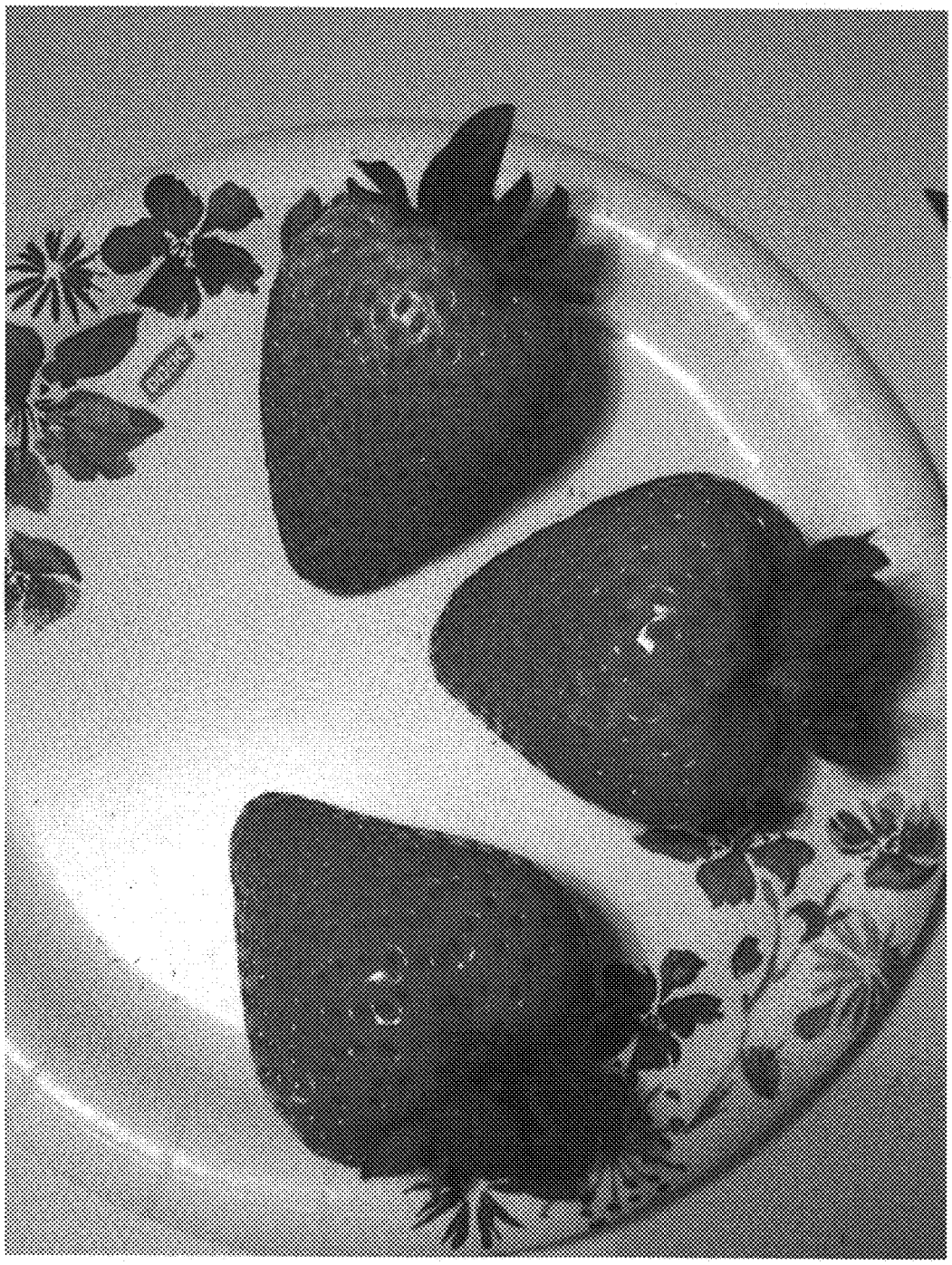
FIG. 2 shows 'LILI' strawberries from early May picking.
Figure 3:
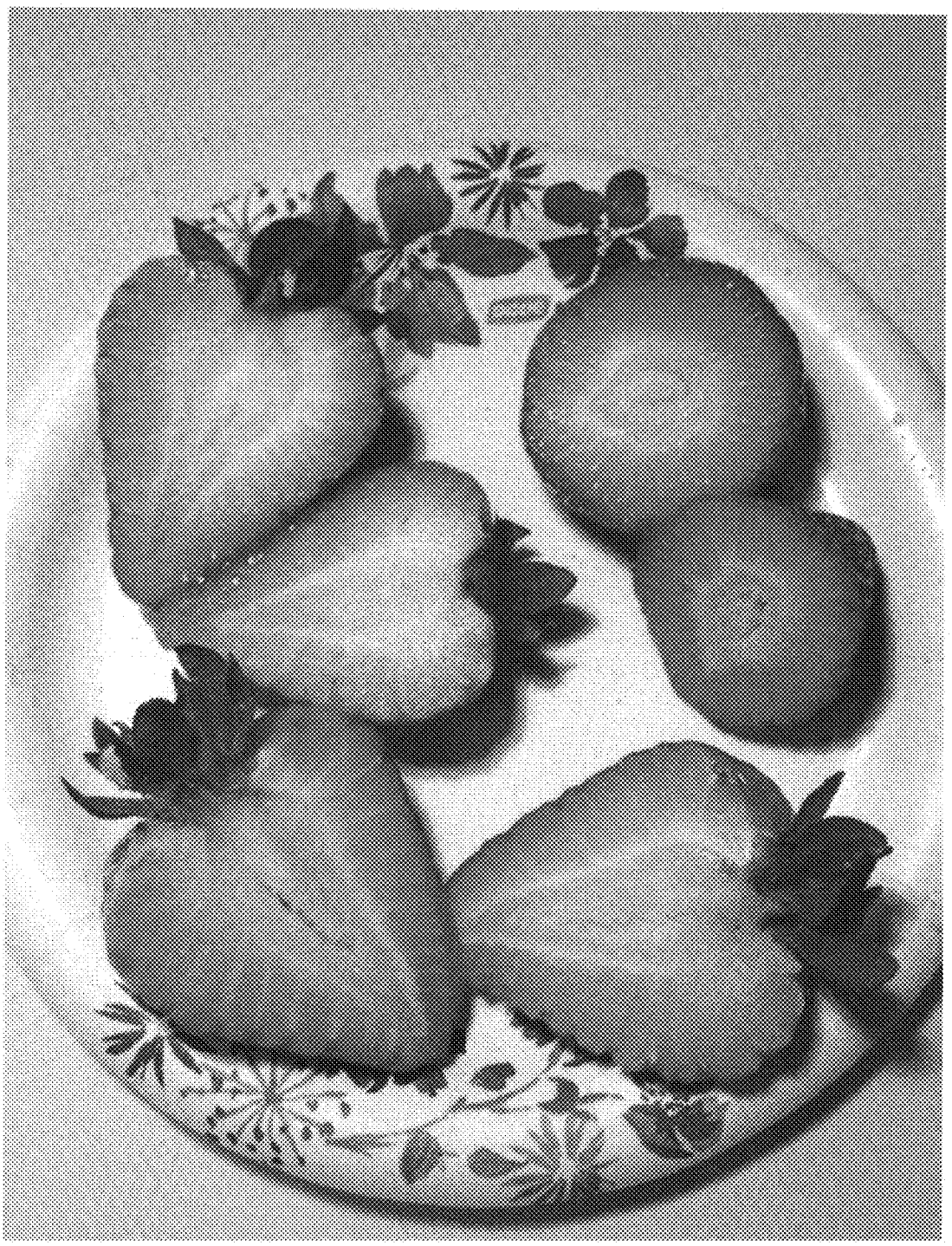
FIG. 3 shows Cross section of early May 'LILI' strawberries.
Figure 4:
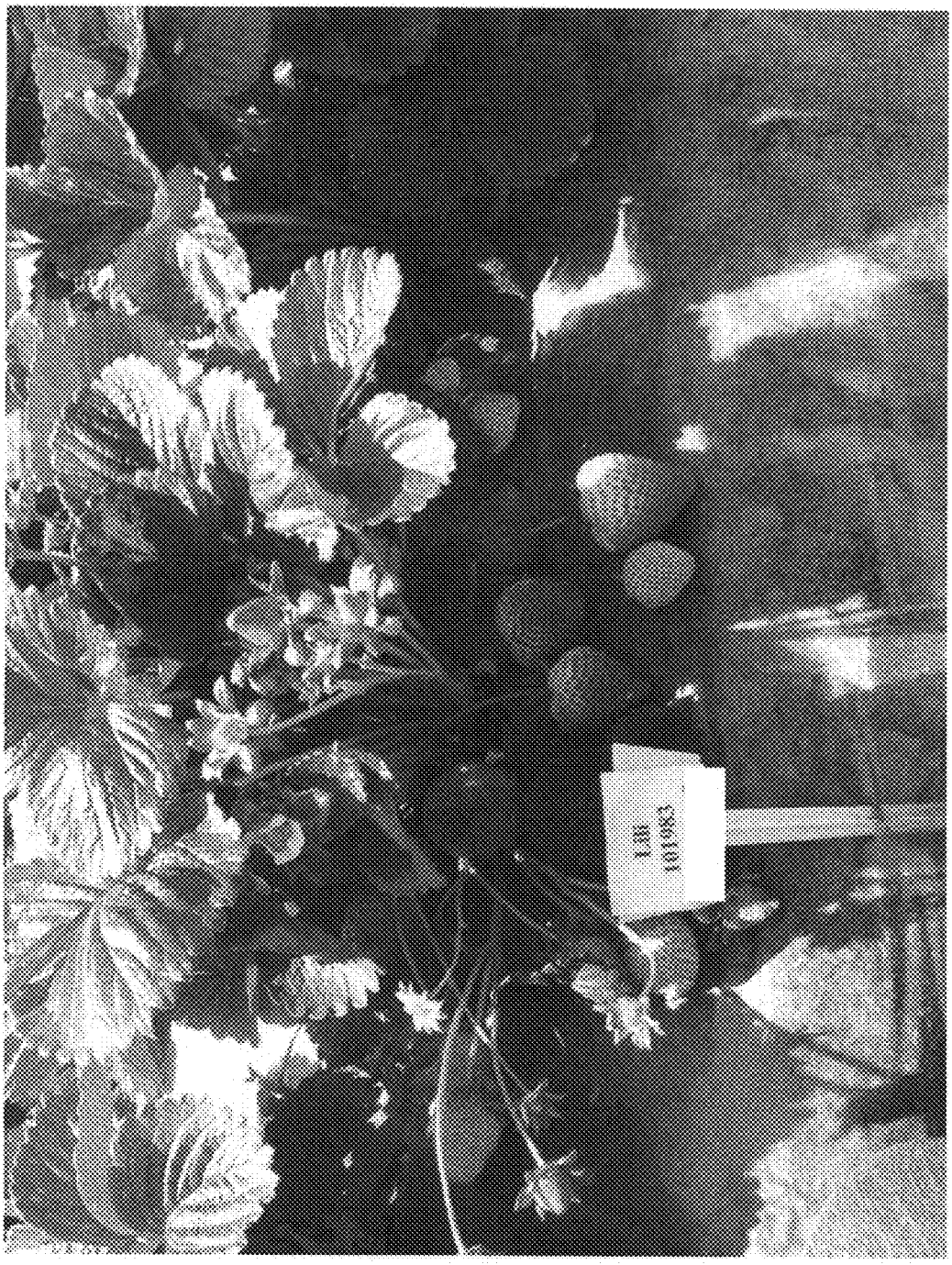
FIG. 4 shows ripe and near-ripe fruits of 'LILI' in May.
Figure 5:
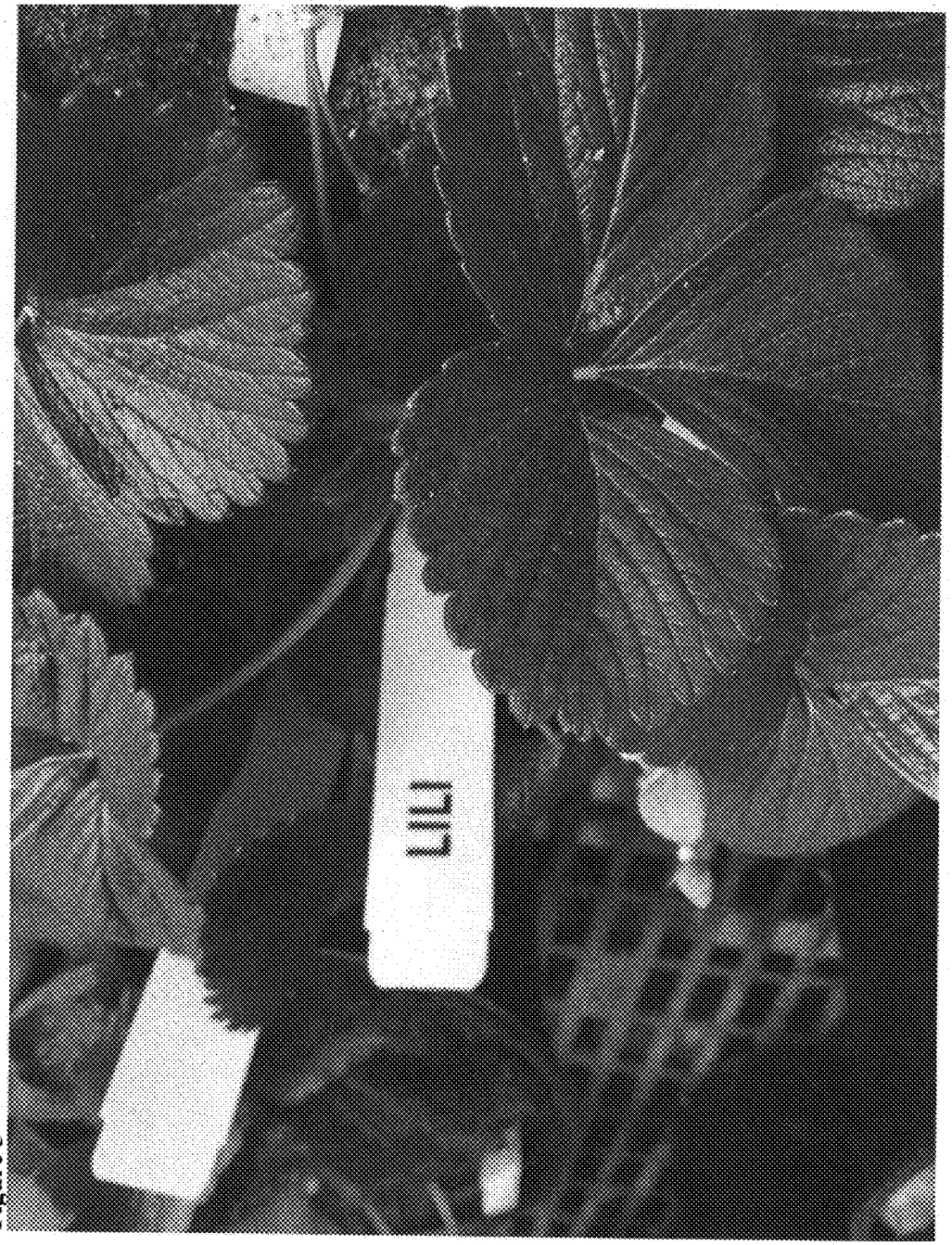
FIG. 5 shows leaves of 'LILI'.
Figure 6:
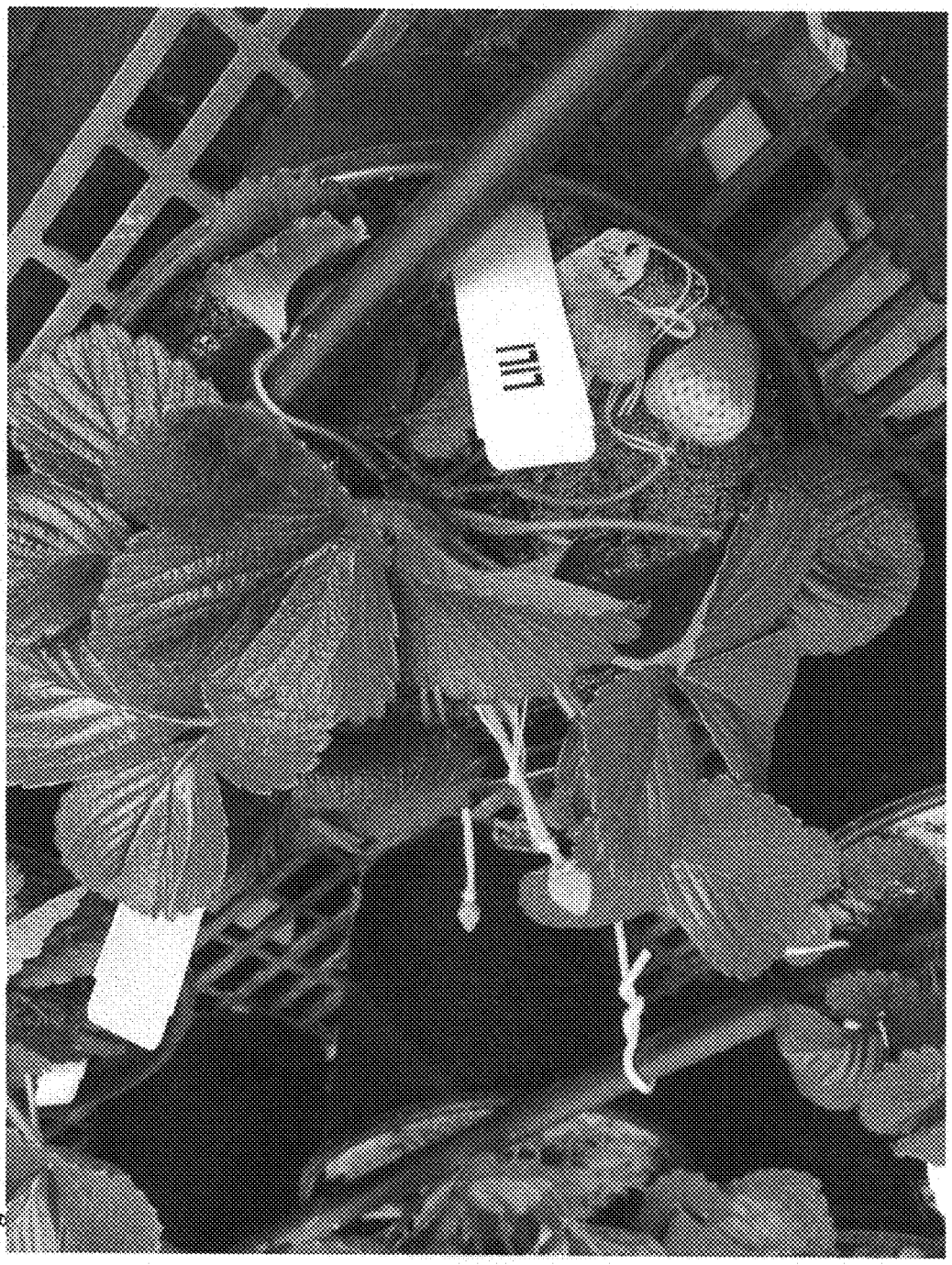
FIG. 6 shows leaves and fruits of 'LILI' plant growing in the greenhouse.
Figure 7:
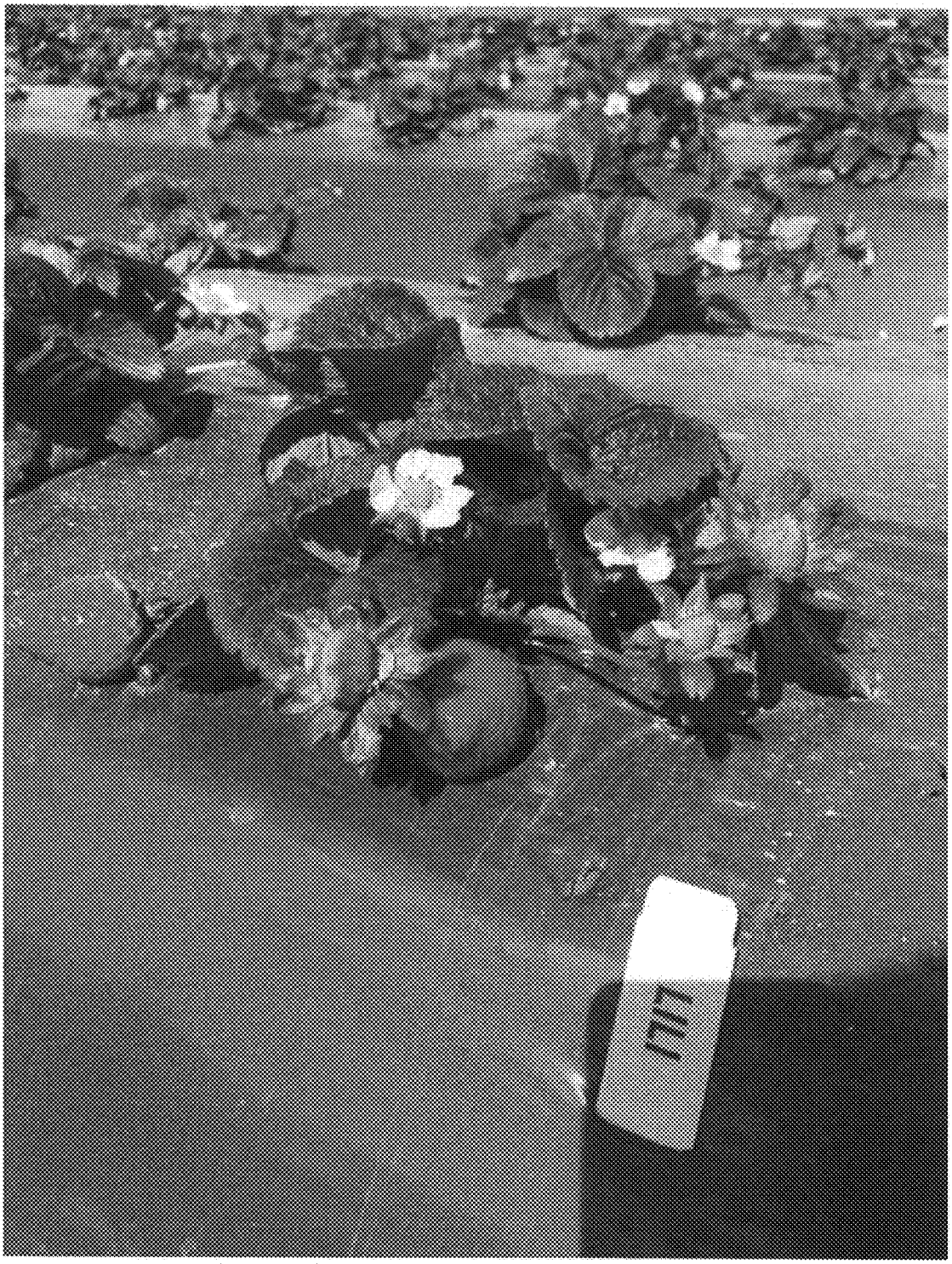
FIG. 7 shows 'LILI' plants growing in the field.

'LILI' has not been observed under all possible environmental conditions, and the phenotype may vary significantly with variations in environment. The following observations, measurements, and comparisons describe this plant as grown at California, when grown in the field, unless otherwise noted. As stated above, the color determination is in accordance with The Royal Horticultural Society Colour Chart, 1995 Edition, except where general color terms of ordinary dictionary significance are used. Plants for the botanical measurements in the present application are annual plants.

Botanical classification: 'LILI' is a fertile hybrid derived from a cross.

Common name: garden strawberry.

General Description:

Plant habit: moderate, coastal climates.

The following description is applied to our plants that are 7 months old as of the time of the measurements.

Classification:

*Species.*—*Fragaria×ananassa.*
*Common name.*—Garden Strawberry.
*Denomination.*—'LILI'.

Plant:

*Height.*—19.0 cm.
*Diameter.*—25.8 cm.
*Habit.*—Globose, upright.
*Density.*—Medium.
*Vigor.*—Strong.

Terminal leaflet:

*Length.*—7.2 cm.
*Width.*—8.5 cm.
*Length/width ratio.*—0.84.
*Shape in cross-section.*—Concave.
*Blistering.*—Low.
*Glossiness.*—Medium.
*Average number of leaflets.*—Exactly 3.
*Color above.*—Dark Green (RHS 137A).
*Color below.*—Green (RHS 139C).
*Shape.*—Orbicular.
*Margin.*—Crenate to Serrate.
*Venation pattern.*—Reticulate.

Petiole:

*Length.*—7.8 cm.
*Width.*—5.7 mm.
*Color.*—Yellow Green (RHS 145A).

Petiolule:

*Length.*—8.0 mm.
*Width.*—2.9 mm.
*Color.*—Yellow Green (RHS 145A).

Stolon:

*Average daughters/plant.*—About one.
*Diameter.*—3.9 mm.
*Color.*—Dark Purple Red (RHS 53A).

Inflorescence:

*Position relative to foliage.*—At same level.
*Average petals/flower.*—5.
*Petal length.*—15.0 mm.
*Petal width.*—15.1 mm.
*Petal length/width ratio.*—0.99.
*Petal shape/base.*—Orbicular.
*Petal apex.*—Round.
*Petal margin.*—Entire.
*Petal spacing.*—Slightly overlapping.
*Petal color.*—White (RHS 157B).
*Corolla.*—33.8 mm.
*Sepal length.*—12.8 mm.
*Sepal width.*—6.4 m.
*Sepal length/width ratio.*—0.70.
*Sepal color.*—Dark Green (RHS 137A).
*Calyx.*—36.0 mm (Diameter relative to corolla: Larger).
*Peduncle.*—9.1.
*Bract frequency.*—Low.

Fruit:

*Fruit truss attitude.*—Prostrate.
*Relative size.*—Large.
*Fruit length.*—41.9 mm.
*Fruit width.*—41.4 mm.
*Fruit length/width ratio.*—1.0.
*Surface color.*—Red (RHS 45A).
*Flesh color.*—Orange Red (RHS 41B).
*Core color.*—White (RHS 155C).
*Shape.*—Predominately conical.
*Average weight/fruit.*—30.3 g.
*Average weight/plant.*—122.9 g.
*Hollow core length.*—32.1 mm.
*Hollow core width.*—10.8 mm.
*Hollow core length/width ratio.*—2.97.
*Insertion of achenes.*—Indented.
*Average achenes/fruit.*—261.
*Firmness of flesh.*—Medium.
*Glossiness.*—Medium.
*Sweetness.*—Medium.

Comparison of 'LILI' to Other Strawberry Varieties

'LILI' is distinctive from other strawberry varieties. The following comparison was made between 'LILI', 'CUPCAKE' (U.S. Plant Pat. No. 23,956) and 'GINZA' (U.S. Plant Pat. No. 23,934), two commercial strawberry varieties adapted to the same general growing region as 'LILI'.

'LILI's' fruiting season approaches peak production early in the production period with heavy fruit load early, ramping into a pronounced peak production period and is not as gradual an increase compared to 'GINZA' which increases very gradually to a delayed late season peak production period. 'LILI' yields more fruit than either 'CUPCAKE' or 'GINZA'. In the propagation nursery 'LILI' produces less than half as many stolons as 'CUPCAKE'.

'LILI' produces very few runners during the fruiting season while 'GINZA' produces a moderate quantity of runners while flowering and producing fruit and 'CUPCAKE' produces an excess of runners during the fruiting season. Because stolons (commonly referred to as "runners") produced by the plant during the fruiting season must be removed from the plant by hand, 'LILI' is significantly more economical for the grower with regard to the labor requirement than is 'GINZA' or 'CUPCAKE'.

The leaf of 'LILI' compared to 'CUPCAKE' is a rounder shape. 'LILI's' middle leaflet of the trifoliate had a length/width ratio of 0.9605, slightly wider the long compared to the middle leaf of 'CUPCAKE's' trifoliate which are elongated and had a length/width ratio of 1.10. This difference between the leaflets of 'LILI' and 'CUPCAKE' is easily discerned visually in the fruiting and nursery fields. For this sampling the 'CUPCAKE' leaflet was less elongated than usually observed. Compared to the middle leaflet of 'GINZA's' trifoliate, 'LILI's' middle leaflet is generally larger than that of 'GINZA' and the 'LILI' leaflet has a curved midrib and is less symmetrical than the smaller leaflet of 'GINZA' with it's straight midrib. The 'GINZA' middle leaflet had a length/width ratio of 0.923. The blade tips of 'LILI's' leaflet are somewhat rounded compared to 'GINZA's' blade tips which are pointed.

The alchenes on the fruit of 'LILI' are located two thirds indented beneath the skin of the fruit and one third above the skin of the fruit and compared to 'GINZA's' alchenes which are very prominent above the surface of the skin. 'LILI's' alchenes are partially above the skin and can be sensed by running a finger across the fruit compared to 'CUPCAKE's' alchenes which are fully indented beneath the skin of the fruit and are not sensed by running a finger across the fruit. The surface of 'LILI's' fruit is somewhat uneven compared to 'CUPCAKE's' fruit surface which is very smooth. The shape of 'LILI's' fruit is conic compared to 'CUPCAKE's' fruit which is mostly globose conic. 'LILI's' conic shaped fruit has a snubbed rounded tip compared to 'GINZA's' conic fruit which has a more pointed tip. The skin of the fruit of 'LILI' resists abrasion and does not easily break open when repeatedly rubbed with moderate pressure of a finger compared to 'CUPCAKE's' skin which does not resist abrasion and will crack open when repeatedly rubbed and when the skin of 'LILI' is compared to 'GINZA's' skin the 'LILI' is lest resistant to abrasion than 'GINZA' which with it's very prominent seeds resists abrasion however occasionally the seeds of 'GINZA' can come loose with repeated rubbing with moderate pressure of a human finger.

When comparing firmness of fruit amongst varieties 'LILI', 'GINZA' and 'CUPCAKE' over 26 samples taken weekly during a 26 week fruit production period the mean firmness value for the group combined was 7.84 with a standard deviation of 2.604. Taken for each variety alone the mean firmness value for 'LILI' over the 26 week period was 9.305 with a range of 5.6 to 18.0; for 'CUPCAKE' the mean firmness was 7.854 with a range of 3.94 to 12.6; for 'GINZA' the mean firmness was 6.365 with a range of 4.0 to 11.75; the fruit of 'LILI' is firmer than the fruits of 'GINZA' and 'CUPCAKE'. The color of the skin of the nearly ripe fruit of 'LILI' when examined at the shoulder of the fruit near and under that calyx has a light greenish yellow color compared to 'CUPCAKE's' shoulder skin color which is less yellowish near the calyx of the nearly ripe 'CUPCAKE' fruit. 'LILI's' nearly ripe fruit shoulder color is a very light greenish yellow compared to 'GINZA's' pure white color at the shoulder near and under the calyx of 'GINZA's' nearly ripe fruit.

When comparing the cull rate over 26 weeks of sampling of fruits discarded for defects for combined varieties 'LILI', 'CUPCAKE', 'GINZA' the mean cull rate was 36.8% with a standard deviation of 0.2063, for 'LILI' the cull rate was 45.3%; for 'CUPCAKE' the cull rate was 36.8%, and for 'GINZA' the cull rate was 28.4%.

When comparing the susceptibility to a type of bruising where black spots appear 3 to 4 days after harvest, 'GINZA' shows less bruising than 'LILI' which shows less bruising than 'CUPCAKE'.

The foliage of 'LILI' is a deep blueish green compared to the color of foliage for 'CUPCAKE' which is a medium green. 'LILI' blueish green foliage color differs in comparison to 'GINZA' foliage color which is a light green.

'LILI' differs from 'GINZA' and 'CUPCAKE' in fruit size. The Fruit size of 'CUPCAKE' in the early season is in the range of 8-10 count per pound while early season 'LILI' fruit size is in the range of 10-14 count per pound. An important difference is the fruit size of 'LILI' remains medium-large throughout the fruit production period and does not "size down" as the harvest period progresses. The 'GINZA' and 'CUPCAKE' produce smaller fruit later in the production period. For this reason 'LILI' is less costly to hand harvest than 'CUPCAKE' and 'GINZA'.

The petiole and leaves of 'LILI' are thicker than the petiole and leaves of 'CUPCAKE' and the plant structure of 'LILI' differs in it's symmetrical upright appearance compared to 'CUPCAKE' with it's wafer thin leaves and delicate long petioles which tends toward lodging in the late season nursery plantings. The 'LILI' plant overall is denser, taller and wider than 'GINZA' as 'GINZA's' plant structure is smaller and more compact than 'LILI'. In the mid season fruiting field 'LILI's' plant structure appears more symmetrical than 'GINZA's' plant structure. The flowers and fruit of 'LILI' grow up and angle outward in a more sideways manner, the peduncle being less turgid compared to the turgid upright peduncle of 'GINZA's' flowers and fruit which develop in a more upward erect manner than that of 'LILI'.

The sepals of the flower of 'LILI' are have single thin pointed tips and 'LILI's' sepals are not overlapping compared to the sepals of 'GINZA' which overlap each other in an alternating pattern of single pointed sepal tips and triple-pointed sepal tips.

The invention claimed is:

1. A new and distinct cultivar of strawberry plant named 'LILI' substantially as shown and described herein.

* * * * *